(12) United States Patent
Lapcevic

(10) Patent No.: US 6,585,720 B2
(45) Date of Patent: Jul. 1, 2003

(54) COLOSTOMY PUMP AND AID

(75) Inventor: Milos Lapcevic, Sydney (AU)

(73) Assignee: Colocare Holdings Pty Ltd, Sydney (AU)

( * ) Notice: Subject to any disclaimer, the term of this patent is extended or adjusted under 35 U.S.C. 154(b) by 12 days.

(21) Appl. No.: 09/142,553

(22) PCT Filed: Mar. 11, 1997

(86) PCT No.: PCT/AU97/00145

§ 371 (c)(1),
(2), (4) Date: Sep. 10, 1998

(87) PCT Pub. No.: WO97/34646

PCT Pub. Date: Sep. 25, 1997

(65) Prior Publication Data

US 2001/0023337 A1 Sep. 20, 2001

(30) Foreign Application Priority Data

Mar. 15, 1996 (AU) .......................................... PN 8724
Dec. 3, 1996 (AU) .......................................... PO 3994

(51) Int. Cl.[7] ........................ A61M 1/00; A61F 5/44
(52) U.S. Cl. ................. 604/540; 604/317; 604/327; 604/332
(58) Field of Search .................. 604/317, 332, 604/334, 27–36, 39, 74–76, 327, 346; 4/340–342, 661

(56) References Cited

U.S. PATENT DOCUMENTS

| | | | |
|---|---|---|---|
| 1,644,257 A | * 10/1927 | Lasker | |
| 4,681,562 A | 7/1987 | Beck | 604/54 |
| 4,713,052 A | 12/1987 | Beck | 604/48 |
| 4,765,907 A | * 8/1988 | Scott | 210/648 |
| 4,798,583 A | 1/1989 | Beck | 604/48 |
| 4,961,726 A | * 10/1990 | Richter | 604/74 |
| 4,964,851 A | * 10/1990 | Larsson | 604/74 |
| 5,009,635 A | 4/1991 | Scarberry | 604/27 |
| 5,011,471 A | * 4/1991 | Miyazaki et al. | 604/22 |
| 5,279,549 A | * 1/1994 | Ranford | 604/34 |
| 5,454,389 A | * 10/1995 | Hubbard et al. | 604/355 |
| 5,484,402 A | * 1/1996 | Saravia et al. | 604/35 |
| 5,503,633 A | * 4/1996 | Saunders et al. | 604/332 |
| 5,718,668 A | * 2/1998 | Arnett et al. | 604/35 |
| 5,738,661 A | * 4/1998 | Larice | 604/180 |
| 5,807,313 A | * 9/1998 | Delk et al. | 604/35 |
| 5,971,956 A | * 10/1999 | Epstein | 604/119 |
| 6,001,086 A | * 12/1999 | Rammacher | 604/327 |

FOREIGN PATENT DOCUMENTS

| | | |
|---|---|---|
| DE | 3441893 | 11/1984 |
| DE | 3438077 | 11/1986 |
| EP | 182248 | 5/1986 |
| FR | 1213896 | 4/1960 |
| NL | 8600585 | 10/1987 |
| WO | WO89 09077 | 10/1989 |

* cited by examiner

*Primary Examiner*—Dennis Ruhl
(74) *Attorney, Agent, or Firm*—Norris McLaughlin & Marcus

(57) ABSTRACT

A waste evacuator to vacate waste products from a stoma having an inlet adapted to seal over the stoma and when operated to vacate waste products from the shortened bowel. The waste evacuator could be battery or manually operated.

12 Claims, 6 Drawing Sheets

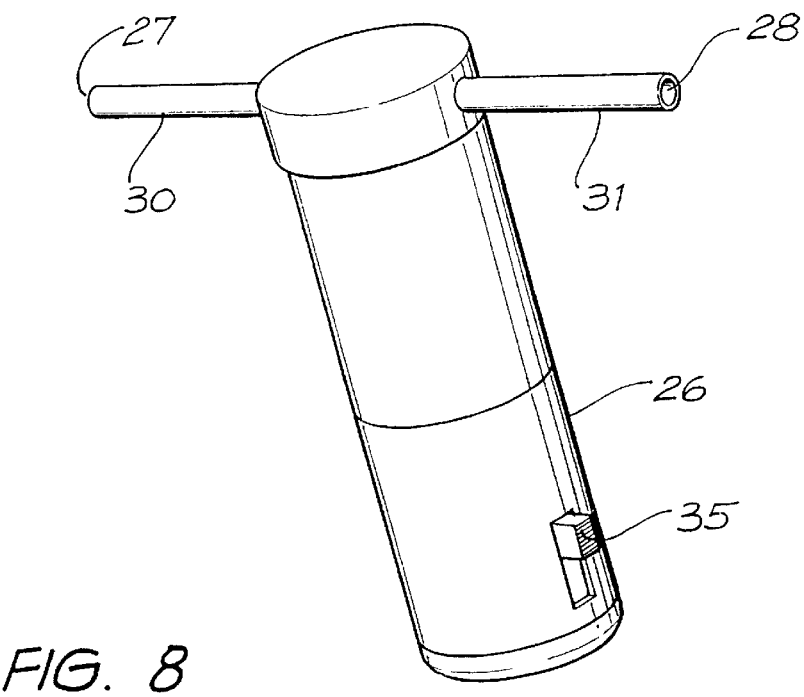
FIG. 8
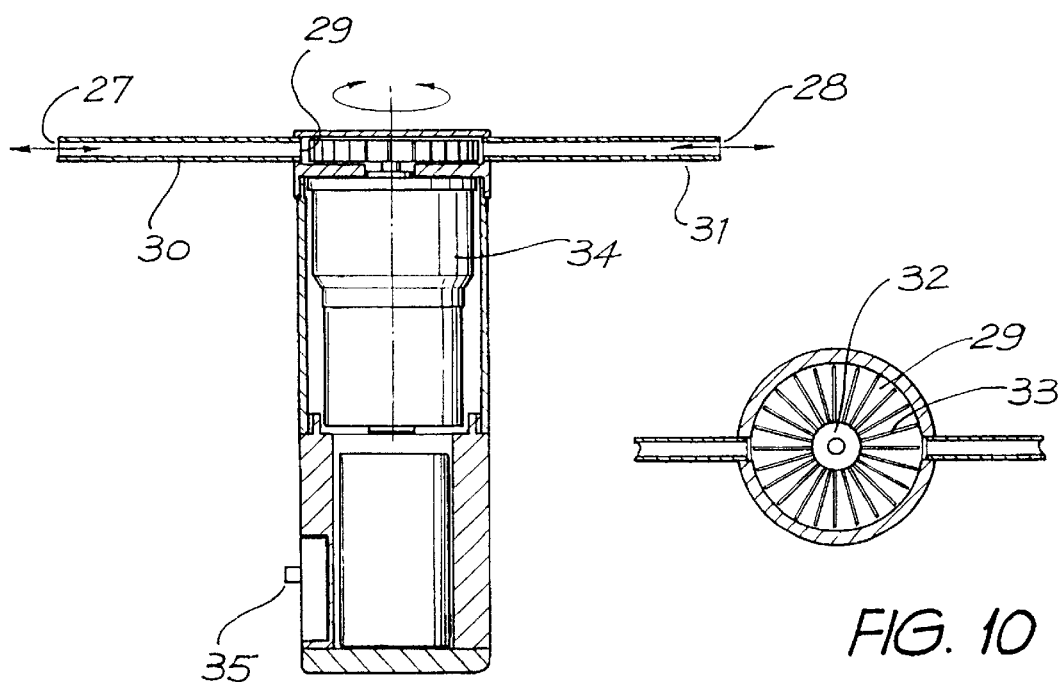
FIG. 9
FIG. 10

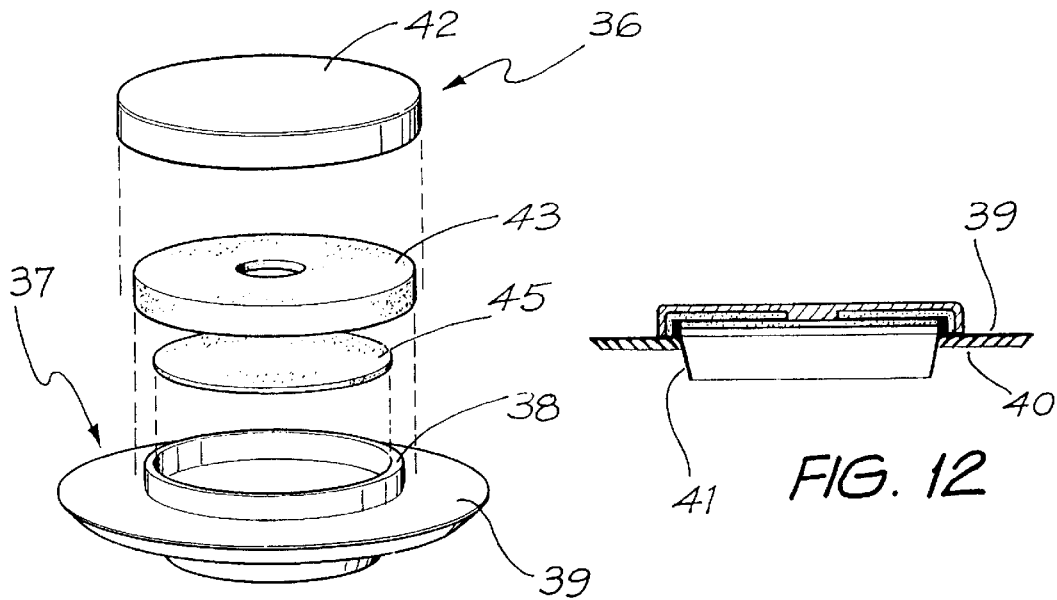
FIG. 11
FIG. 12
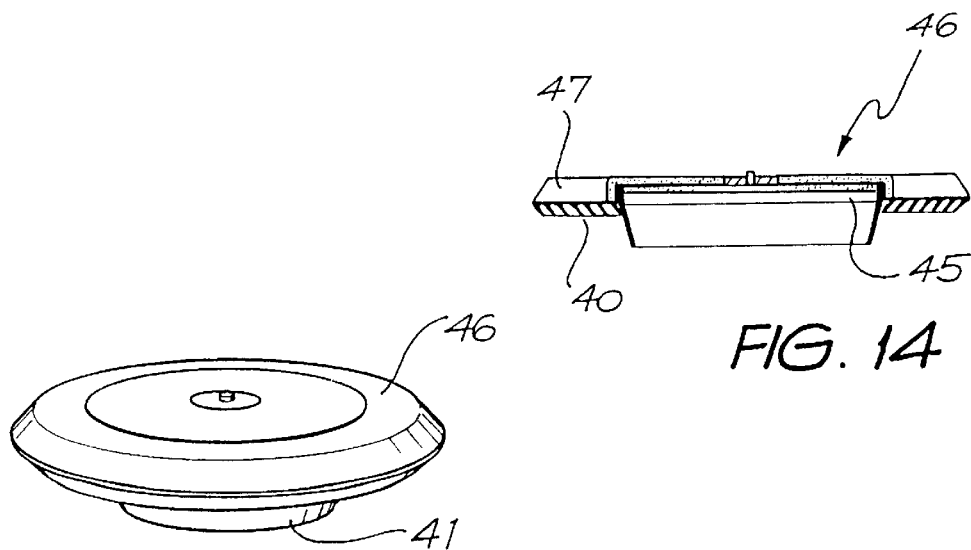
FIG. 13
FIG. 14

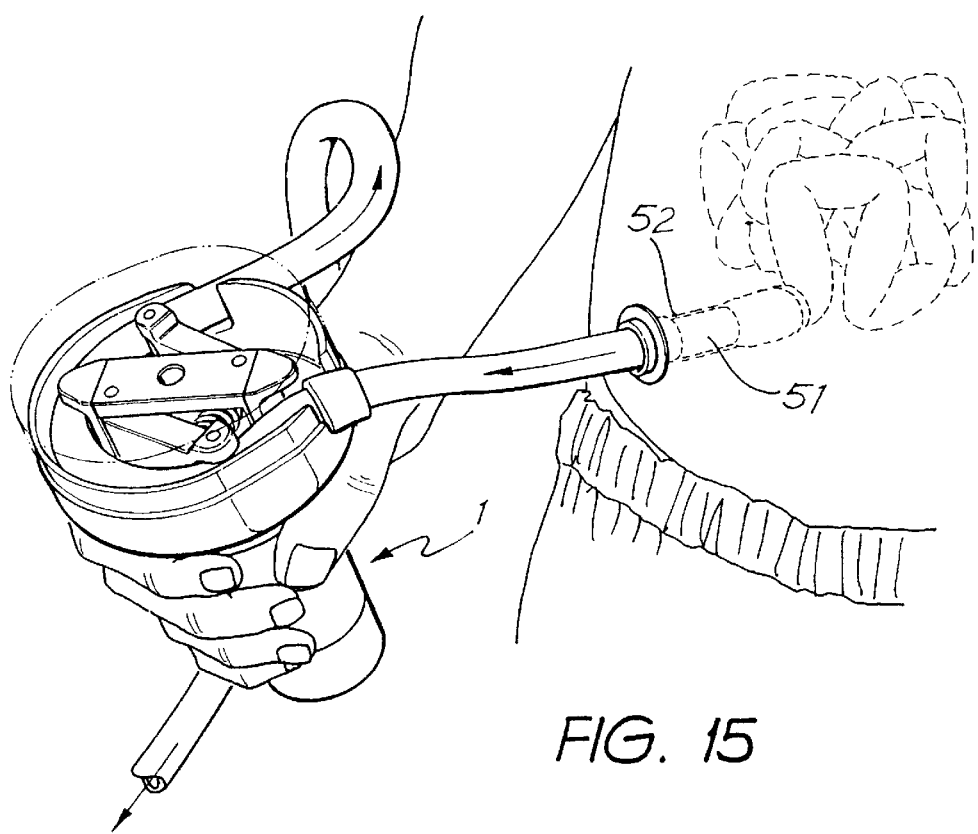
FIG. 15
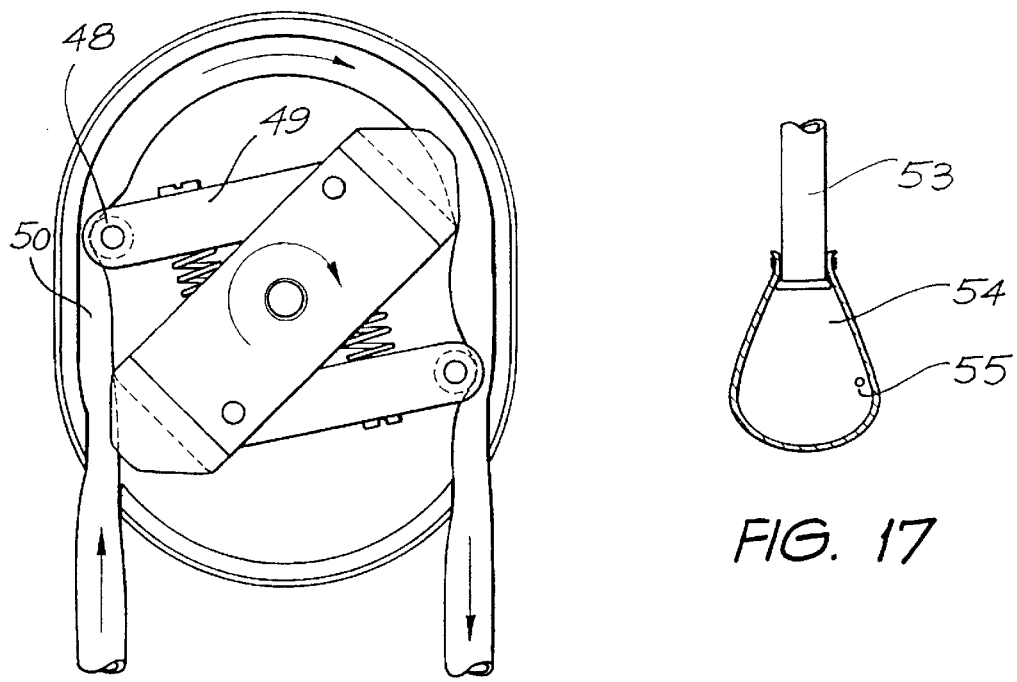
FIG. 16
FIG. 17

COLOSTOMY PUMP AND AID

The present invention relates to an aid for patients who have undergone a colostomy, and in particular to a means to vacate and a method of vacating the waste products from patients who have undergone a colostomy, and an improved colostomy flange and plug cover.

As a result of medical problems it is sometimes necessary for a patient to undergo a colostomy, resulting in the production of a stoma which may be temporary or permanent. As a result of the colostomy the body's waste is removed through the stoma. To assist in the comfort of the ostimist, and the removal of the waste, a wafer (1), as shown in FIG. 1, is connected to the stoma.

This wafer is provided with a sealing lip to which the various appliances, such as waste collection pouches, necessary for the well being of the ostimist is connected. The only existing means of collecting waste from the ostimist is by means of collection pouches, which must be removed and replaced with a fresh collection bag. Also it is necessary to replace the wafers at the required intervals. This is usually a messy and time consuming operation, for the ostimist, as less viscous wastes leak from the stoma.

The present invention seeks to provide an improved apparatus for vacating waste products from the stoma by providing a colostomy evacuator, which is adapted to seal over the stoma and when operated to vacate the waste products held in the shortened bowel. This would lessen or remove the need for the use of a collection pouch. Further the ostimist, could vacate the less viscous wastes, from the shortened bowel, before the wafer is removed to make the replacement of the wafer cleaner and easier.

In one broad form the invention comprises a waste evacuator for vacating waste products from the stoma comprising an inlet adapted to seal over the stoma;
an outlet;
a motor;
a housing; and
an drive means, wherein the motor operates the drive means, so that when the inlet is sealed over the stoma, the drive means draws the waste products held in the shortened bowel, through the inlet and out of the outlet of the evacuator.

In another form the invention comprises a method of vacating waste from the stoma of an ostimist comprising the steps of placing an inlet of a waste evacuator over or in the stoma, to substantially seal the stoma and activating the evacuator to remove waste from the stoma.

In a further form the present invention seeks to provide a waste evacuator for vacating waste products from the stoma comprising
housing having an opposed inlet and outlet, said inlet being adapted to seal over the stoma;
a motor; and
an impeller located in said housing and driven by said motor, said impeller having a plurality of radially extending vanes, which force material through the pump.

In another form the invention comprises a colostomy flange adapted to be secured in position on the stoma, comprising:
a flange member having an upper and a lower side, with a central opening therethrough;
a tube extending from the underside of said flange member;
gill members located on the underside of the flange members; and
a sealing lip located on the upper surface of the flange member, adapted to engage in a sealing manner with a cover.

Preferably said cover comprises:
a central valve;
an outer protective layer, and
inner layer of odour absorbing and noise proofing material The present invention will now be described by way of example with reference to the accompanying drawings, in which:

FIG. 8 illustrates a view of a pump according to another embodiment of the present invention;

FIG. 9 illustrates a side sectional view of the pump shown in FIG. 8 of the accompanying drawings;

FIG. 10 illustrates a sectional plan view of the end of the pump shown in FIG. 9 of the accompanying drawings, with the end cover removed;

FIG. 11 illustrates an exploded view of a flange and cover according to another embodiment of the present invention;

FIG. 12 illustrates a cross-sectional view of the flange shown in FIG. 11;

FIG. 13 illustrates a perspective view of a flange and cover according to another embodiment of the present invention;

FIG. 14 illustrates a cut away side view of a flange and cover according to another embodiment of the present invention;

FIG. 15 illustrates the use of another pump according to another embodiment of the present invention;

FIG. 16 illustrates a plan view of the pump in FIG. 15 of the accompanying drawings, with the cover removed; and FIG. 17 illustrates a collection attachment, useable with embodiments of the present invention, to collect small quantities of waste.

Figure 3:
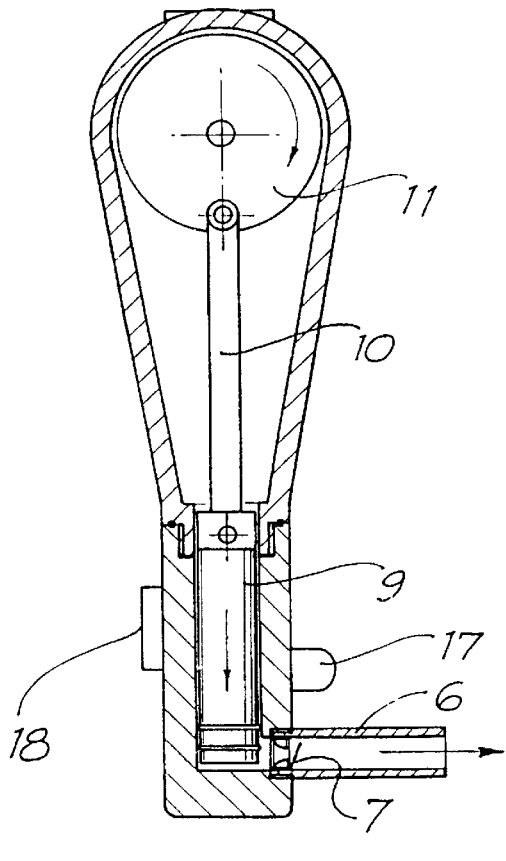
FIG. 3 illustrates a sectional elevation view of the pump shown in FIG. 2 of the accompanying drawings.
Figure 4:
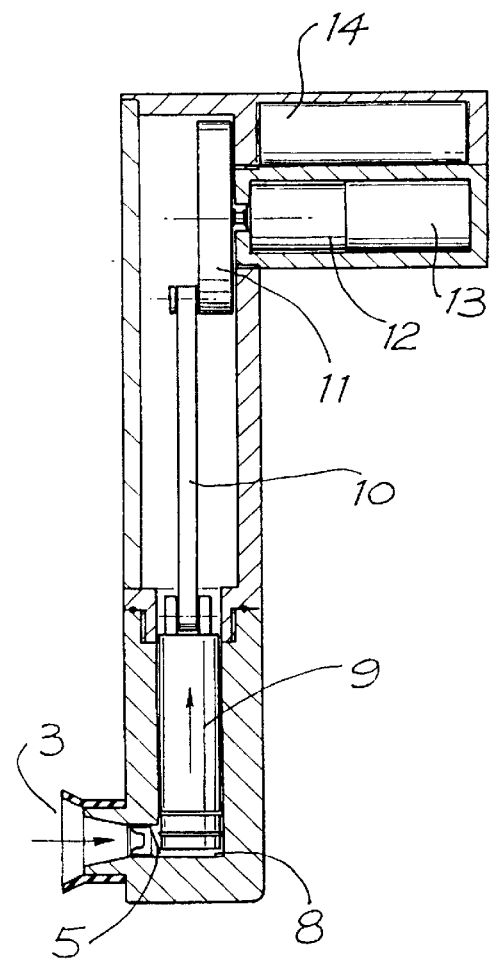
FIG. 4 illustrates another sectional view of the pump shown in FIG. 2 of the accompanying drawings.
Figure 5:
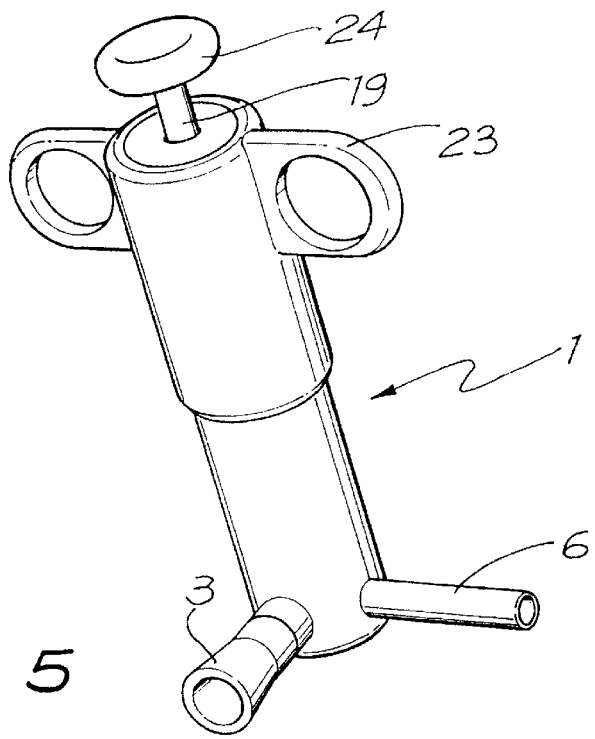
FIG. 5 illustrates a plan view of a manually operated pump according to another embodiment of the present invention.
Figure 7:
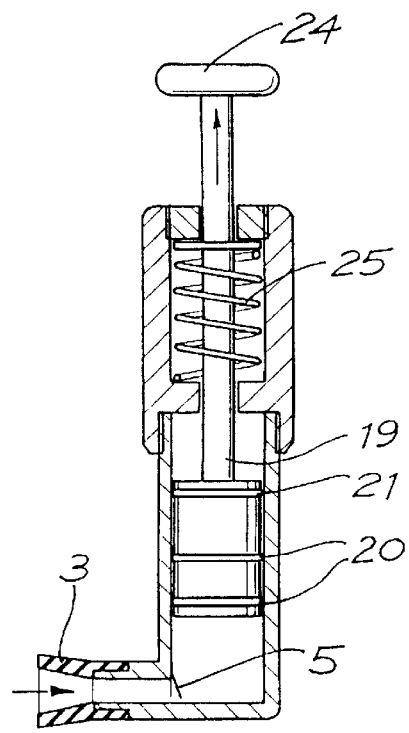
FIG. 7 illustrates a further sectional view of the pump shown in FIG. 5.

A pump according to the present invention can be in two forms; battery operated, shown in FIGS. 2–4, 8–10 and 15–16, or manually operated, shown in FIGS. 5 & 7. The actual method of use of both forms being substantially identical.

Figure 2:
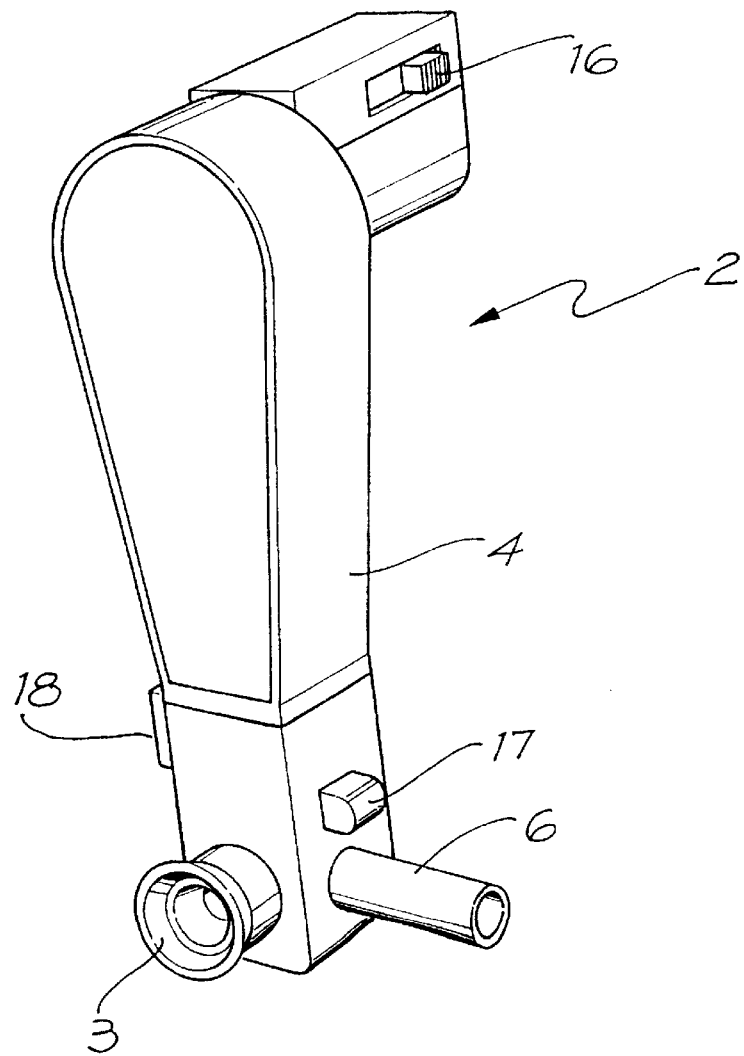
FIG. 2 illustrates a prospective view of a pump according to one embodiment of the present invention.

One embodiment of a battery operated pump (2) is shown in FIGS. 2 to 4. The pump (2) comprises a hand held body (4), having an inlet (3) with a non return inlet valve (5) of any suitable type, and an outlet (6) with a non return discharge valve (7) of any suitable type. Both the inlet (3) and the outlet (6) are in communication with the cylinder chamber (8). A drive piston (9) is slideably mounted in the cylinder chamber (8), and forms a labyrinth seal with the cylinder wall. A connecting rod (10) is pivotally connected, at one end, to the piston (9) and at the other end to a fly wheel (11). The fly wheel (11) is connected via a gear box (12) to an electric motor (13), which is powered by the battery (14).

Figure 1:
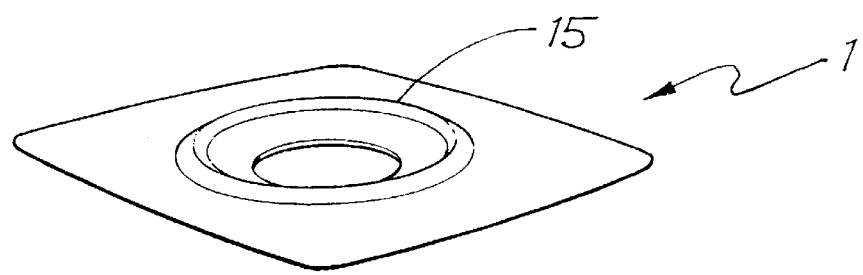
FIG. 1 shows a wafer to which can be attached the various appliances, such as waste collection pouches, necessary for the well being of the ostimist.

To use the pump an ostomist first removes the plug (not shown) on the wafer (1) as shown in FIG. 1 and using one hand places the inlet (3) of the pump (2) into sealing engagement with the sealing lip (15) of the wafer (1), and operates the switch (16). The piston (9) reciprocates along the cylinder (8) as the fly wheel (11) rotates, whereby during the suction stroke, the outlet valve (7) is closed and the inlet valve (5) is open and waste material is drawn through the stoma into the cylinder chamber (8), and when the piston (9) moves in the discharge stroke, the inlet valve (5) closes and the outlet valve (7) opens, whereby the waste drawn into the cylinder chamber (8) is discharged through the outlet (6). The pumping is continued until sufficient waste has been vacated from the shortened bowel, and then the wafer (1) is sealed.

A hand stop (17) is located on the hand held body (4), to assist in the useability of the pump and a potentiometer (18) is located on the hand held body (4) to vary the speed of the motor and hence the suction head.

In a variation of the pump of this embodiment (not shown), the outlet (6) is aligned with the cylinder chamber (8) and has the same internal diameter. To assist in cleaning of the pump, a lining tube is inserted into the cylinder chamber (8) to form a lining along which the piston (9) moves and also which forms a flexible outlet of any required length.

Figure 6:
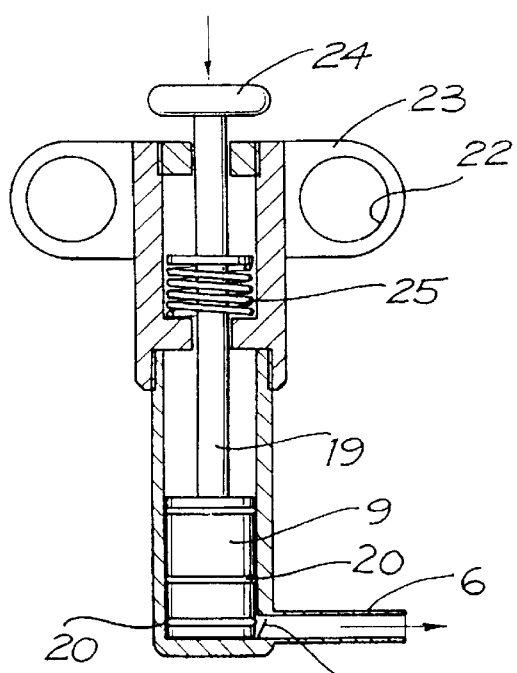
FIG. 6 illustrates a sectional elevation view of the pump shown in FIG. 5 of the accompanying drawings.

Another embodiment, in the form of a manually activated pump, is shown in FIGS. 5, 6 & 7. This pump operates in a similar manner to that of the battery operated pump, described previously.

However the piston (9) is operated manually. A drive shaft (19) is connected to the piston (9), which has, as seals, a system of two elastomeric o-rings (20) and a nylon or similar plastics o-ring (21) located in respective grooves around the piston (9).

To use the pump, an ostomist places a finger (not shown) in the openings (22) in the wings (23), and depresses the head (24) of the drive shaft (19) driving the piston (9) in the discharge stroke, against the spring means (25). When the head (24) is released the spring means (25) moves the piston (9) in the suction stroke. Conversely the head (24) could be pulled to provide the suction stroke with the spring means supplying the discharge stroke.

A pump according to a further embodiment of the present invention is shown in FIGS. 8–10. The pump (1) comprises a hand held body (26), having located at one end an inlet/outlet (27) and an outlet/inlet (28). Both the inlet and the outlet are in communication with a circular cavity (29); the inlet and outlets (27 & 28) are in the form of pipes (30 & 31). An impeller (32) having a plurality of radially extending vanes (33) is mounted therein in sealing engagement with the walls of the pump chamber (29). The pump (1) is controlled by a bi-directional motor (34), with a forward or reverse switch (35).

To use the pump an ostomist first removes the cover (36) on the colostomy flange or wafer (37), as shown in FIGS. 11–14. The pump (1) is filled with a faeces soften fluid and using one hand places the inlet/outlet (27) of the pump into sealing engagement with the sealing lip (38) of the flange (37), and operates the switch (35), pumping the faeces softening fluid into the stoma. The pump (1) direction is then reversed and waste material is drawn through the stoma by the rotating impeller (32) and discharged through the outlet/inlet (28). The pumping is continued until sufficient waste has been vacated from the shortened bowel, and then the flange (37) is sealed.

A potentiometer can be located on the hand held pump to vary the speed of the motor and hence the suction head. The pump is so designed that it operates at an medically approved range of pressures. Preferably the pump is waterproof and can be constructed of any suitable material such as PTFE (polytetrafluoroethylene).

An embodiment of an improved flange or wafer (37) is shown in FIGS. 11 to 14. The wafer (37) comprises a circular flange member (39), although the flange could be any desirable shape, having a plurality of gill members (40) located in concentric circles on the underside thereof. The gill members (40) are preferably tapered to assist in their flexibility and the adherence of the wafer (37) to the skin of the ostomist. To allow for breathing of the skin beneath the wafer (37), the flange member (39) is perforated.

Extending from the underside of the wafer (37) is a small tube (41), which engages in the stoma of the ostomist. This tube is tapered and is made in various diameters so as to fit the various size stoma.

A cover (36) snap fits on to the sealing lip (38) of the wafer (37). The cover (36) comprises an outer protective layer (42). and an inner odour absorbing and noise proofing layer (43). Preferably this layer contains activated charcoal. The cover (36) has a central opening (44) which is fitted with a valve, which in this case is a flap valve (45).

Thus when the gases build up in the shortened bowel, particularly during activities such as sport, the ostomist easily opens the valve, by a gentle pressure and release the built up gases.

A cover according to another embodiment of the present invention is shown in FIGS. 13 and 14. The wafer (37) and cover (46) are the same as the previous embodiment. However the cover (46) has a soft plastics storage section (47) able to expand to store gases which build up in the shortened bowel. Such a cover would be useful for the ostimist in business meetings when it is necessary to release the pressure of the built up gases in the shortened bowel without releasing the gases to the immediate environment.

A pump according to yet a further embodiment is shown in FIGS. 15 and 16, in which the pump 1 is in the form of a "flow inducer" type pump, in which the fluids, to be transported, are forced by rollers (48) which rotate on the arms (49) through the flexible tubing (50), as the rollers (48) seal the tubing (50) against the wall of the pump as they rotate around the pump. This embodiment has the advantage in that the wastes bring vacated are separated from the rotor of the pump, and that the tubing can easily be cleaned by flushing or easily and cheaply replaced.

This pump can be used in the same manner as the previous embodiments, or can have an inlet (51) which is inserted into the stoma (52) as shown in FIG. 15.

Additionally the pumps could be a small unit and have at their outlet (53) a disposable storage unit (54). This unit has a vent hole (55) located therein. The ostimist places his/her finger on the hole and adjusts the suction and filling of the disposable storage container (54). This type of unit can be used for small emergencies when a small leak or the like occurs.

In another form not shown the outlet of the pump could be connected a larger disposable storage container similar to that shown in FIG. 17.

The pumps of the present invention are so designed that they operate at a medically approved range of pressures. Preferably the pump is waterproof and can be constructed of any suitable material such as PTFE (polytetrafluoroethylene).

It should be obvious to people skilled in the art that modifications and alterations can be made to the above described embodiments without departing from the scope or the spirit of the present invention.

What is claimed is:

1. A waste evacuator for vacating waste products from a stoma comprising an inlet having a flange means for providing a seal over the stoma;
   an outlet;
   a motor; and
   a drive means, having a chamber, for drawing the waste products held in a shortened bowel through the inlet and out of the outlet of the evacuator when the inlet is sealed over the stoma,
   said outlet is connected to the chamber for discharge of the waste products contained in the chamber,
   wherein the motor operates said drive means.

2. A waste evacuator according to claim 1 wherein said chamber is cylindrical and said drive means comprises a piston which slides along the cylindrical chamber, in a substantially sealing engagement.

3. A waste evacuator according to claim 2, wherein the piston is connected by a drive rod to a fly wheel, said fly wheel being driven by the motor.

4. A waste evacuator according to claim 2, wherein the inlet and outlet are connected to a side wall of the cylindrical chamber.

5. A waste evacuator according to claim 1, wherein the motor is powerable by a battery.

6. A waste evacuator according to claim 1, wherein the inlet of the evacuator is insertable into the stoma.

7. A waste evacuator for vacating waste products from a stoma comprising an inlet adapted to seal over the stoma;
   an outlet,
   a motor; and
   a drive means for drawing the waste products held in a shortened bowel through the inlet and out of the outlet of the evacuator when the inlet is sealed over the stoma,
   said drive means comprises a piston which slides along a lining of a cylindrical chamber, in a substantially sealing engagement,
   said outlet is connected to the cylindrical chamber for discharge of the waste products contained in the cylindrical chamber,
   wherein a plastic tube residing in the outlet forms the lining in the cylindrical chamber against which the piston slides; and
   wherein the motor operates the drive means.

8. A waste evacuator for vacating waste products from a stoma comprising an inlet adapted to seal over the stoma;
   an outlet;
   a motor; and
   a drive means for drawing the waste products held in a shortened bowel through the inlet and out of the outlet of the evacuator;
   wherein the drive means comprises at least two arms which are rotated within a substantially circular chamber having an outer wall;
   a flexible plastic tubing which lies in the chamber, forming the inlet and the outlet of the evacuator, and is compressed against the wall of the chamber by the at least two arms,
   wherein as the arms rotate within the chamber, the arms move along said flexible plastics tubing, which moves waste material along said flexible plastics tubing by flow induction,
   wherein the motor operates said drive means when the inlet is sealed over the stoma.

9. A waste evacuator for vacating waste products from a stoma comprising an inlet adapted to seal over the stoma;
   an outlet;
   a motor; and
   a drive means for drawing the waste products held in a shortened bowel through the inlet and out of the outlet of the evacuator;
   wherein the drive means comprises at least two arms which are rotated within a substantially circular chamber having an outer wall;
   said at least two arms are pivotally connected to a central member and are biased by spring means between said central member and each arm to compress a flexible plastic tubing against the wall of the chamber,
   said flexible plastics tubing which lies in the chamber, forming the inlet and the outlet of the evacuator, and is compressed against the wall of the chamber by the at least two arms,
   wherein as the arms rotate within the chamber, the arms move along said flexible plastics tubing, which moves waste material along said flexible plastics tubing by flow induction,
   whereby the motor operates the drive means when the inlet is sealed over the stoma.

10. A waste evacuator for vacating waste products from a stoma comprising an inlet adapted to seal over the stoma;
    an outlet;
    a motor; and
    a drive means for drawing the waste products held in a shortened bowel through the inlet and out of the outlet of the evacuator,
    wherein the drive means comprises at least two arms which are rotated within a substantially circular chamber having an outer wall;
    said at least two arms are pivotally connected to a central member and are biased by spring means between said central member and each arm to compress a flexible plastic tubing against the wall of the chamber,
    said flexible plastic tubing which lies in the chamber, forming the inlet and the outlet of the evacuator, and is compressed against the wall of the chamber by said at least two arms,
    wherein as said at least two arms rotate within the chamber, said at least two arms move along said flexible plastic tubing which moves waste material along said flexible plastic tubing by flow induction, wherein each arm has a roller which bears on said flexible plastic tubing,
    whereby the motor operates the drive means when the inlet is sealed over the stoma.

11. A waste evacuator for vacating waste products from a stoma, comprising:
    an inlet adapted to seal over the stoma;
    an outlet;
    a motor; and
    a drive means for drawing the waste products held in a shortened bowel through the inlet and out of the outlet of the evacuator when the inlet is sealed over the stoma, said drive means comprising an impeller located in a circular chamber and driven by said motor, said impeller having a plurality of radially extending vanes which, when rotated in said circular chamber, force waste material through the evacuator.

12. A waste evacuator according to claim 11, wherein the motor is reversible.

* * * * *